United States Patent [19]

Merger et al.

[11] Patent Number: 4,965,362

[45] Date of Patent: Oct. 23, 1990

[54] JOINT PREPARATION OF 3-DIALKYLAMINOPROPIONITRILES, BIS-(2-CYANOETHYL) ETHER AND, IF DESIRED, ETHYLENE-CYANOHYDRIN

[76] Inventors: Franz Merger, 25 Max-Slevogt-Strasse, 6710 Frankenthal; Wolfgang Harder, 16 Bergwaldstrasse, 6940 Weinheim; Peter Hettinger, 4 Sievertstrasse, 6802 Ladenburg; Claus-Ulrich Priester, 18 Ungsteinaer Strasse; Dieter Franz, 75 Horst-Schork-Strasse, both of 6700 Ludwigshafen; Dieter Voges, 113 Speyerer Strasse, 6800 Mannheim 1, all of Fed. Rep. of Germany

[21] Appl. No.: 376,373

[22] Filed: Jul. 6, 1989

[30] Foreign Application Priority Data

Jul. 23, 1988 [DE] Fed. Rep. of Germany ....... 3825119

[51] Int. Cl.$^5$ ................. C07C 253/18; C07D 295/145
[52] U.S. Cl. .................................... 546/246; 548/569; 558/450; 558/451; 558/452
[58] Field of Search ....................... 558/450, 452, 451; 548/569; 546/246

[56] References Cited

U.S. PATENT DOCUMENTS

| | | |
|---|---|---|
| 2,404,164 | 7/1946 | Carpenter . |
| 2,425,693 | 8/1947 | Cook et al. . |
| 2,448,979 | 9/1948 | Hopff et al. . |
| 2,459,062 | 1/1949 | Cook et al. . |
| 2,459,088 | 1/1949 | Moss et al. . |
| 2,816,130 | 12/1957 | Selcer et al. . |
| 4,709,072 | 11/1987 | Merger et al. . |

FOREIGN PATENT DOCUMENTS

| | | |
|---|---|---|
| 1189975 | 4/1965 | Fed. Rep. of Germany . |
| 81-8550 | 10/1983 | Japan . |
| 1007690 | 10/1965 | United Kingdom . |

OTHER PUBLICATIONS

Chemical Abstracts, vol. 68, (1968), No. 29272e.

*Primary Examiner*—Joseph Paul Brust

[57] ABSTRACT

3-Dialkylaminopropionitriles

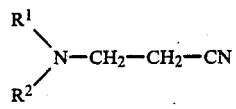

I where $R^1$ and $R^2$ are each $C_1$-$C_4$-alkyl which may furthermore be bonded to form a 5-membered or 6-membered ring, bis-(2-cyanoethyl) ether II

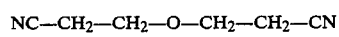

II and, if desired, ethylenecyanohydrin III

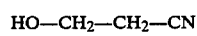

III are prepared jointly by a process in which (a) acrylonitrile and water are reacted in the presence of a base at from 60° to 150° C. to give a mixture of acrylonitrile, water and bis-(2-cyanoethyl) ether II, the base being a mineral base, a quaternary nitrogen base or a mixture of these, (b) this mixture is reacted at about 0°–50° C. with a dialkylamine of the general formula IV

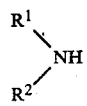

IV to give a mixture of water, a dialkylaminopropionitrile I and bis-(2-cyanoethyl) ether II, and this mixture is separated into its components and (c) if desired, the ether II obtained in proces stage (b) or an aqueous solution of this ether and/or the reacted mixtures containing this ether and obtained from process stage (a) or (b) is allowed to react at from 50° to 150° C. with the dialkylamine IV to give a mixture of a 3-dialkylaminopropionitrile I and ethylenecyanohydrin III, and, if desired, the said mixture is separated into its components.

8 Claims, No Drawings

JOINT PREPARATION OF 3-DIALKYLAMINOPROPIONITRILES, BIS-(2-CYANOETHYL) ETHER AND, IF DESIRED, ETHYLENE-CYANOHYDRIN

The present invention relates to a novel process for the joint preparation of 3-dialkylaminopropionitriles of the general formula I

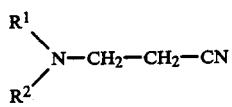

where $R^1$ and $R^2$ are each $C_1$-$C_4$-alkyl which may furthermore be bonded to form a 5-membered or 6-membered ring, bis(2-cyanoethyl) ether II $$NC-CH_2-CH_2-O-CH_2-CH_2-CN \qquad II$$

and, if desired, ethylenecyanohydrin III $$HO-CH_2-CH_2-CN \qquad III.$$

Compounds I to III are of considerable interest as intermediates. Dialkylaminopropionitriles I are used in the preparation of disinfectants, wetting agents and plasticizers. Bis-(2-cyanoethyl) ether II is an important solvent, for example for cellulose finishes, is used for extracting aromatics from crude oil and is an intermediate for the preparation of plasticizers for PVC. Ethylenecyanohydrin III has a wide range of applications as an intermediate for the preparation of dyes, crop protection agents, drugs and plastics.

The preparation of the individual products I, II and III is known. 3-Dialkylaminopropionitriles I are generally prepared by subjecting dialkylamines to an addition reaction with acrylonitrile (U.S. Pat. No. 2,459,062 and U.S. Pat. No. 2,459,088). The nitriles I can readily be obtained in this manner.

In contrast, a number of difficulties have to be overcome in the industrial preparation of bis-(2-cyanoethyl) ether II. Compound II forms in the presence of bases by the addition reaction of one molecule of water with two molecules of acrylonitrile, in accordance with equation (1).

$$2NC-CH=CH_2 + H_2O \longrightarrow \qquad (1)$$
$$NC-CH_2-CH_2-O-CH_2-CH_2-CN$$
$$II$$

However, this reaction leads to the formation of brown byproducts which can be separated off only with very great difficulty, if at all, and greatly diminish the value of the product. A number of processes have been developed to overcome these difficulties but all of these processes have serious deficiencies.

DE-B 11 89 975 describes a process in which acrylonitrile is converted into the ether II in the presence of an excess of from 100 to 400 mol % of water. Since, in this process, only 83% of the acrylonitrile is converted, it has to be recovered by distillation and recycled into the process. Furthermore, purification of the ether II is very expensive, since the distillation gives rise to fractions which have to be recycled, and the space-time yield is low. Consequently, this process is uneconomical.

According to U.S. Pat. No. 2,816,130, the ether II is prepared using an acrylonitrile/water ratio of not more than 4:1. Apart from the fact that this process is unacceptable because of its poor yield (50% of theory), it also has the disadvantage that large amounts of aqueous acrylonitrile solution have to be worked up by distillation, a disadvantage also possessed by the previous processes for the preparation of II. Apart from the additional costs incurred in the handling and distillative working up of these acrylonitrile solutions, these steps present problems in that the acrylonitrile is not toxicologically safe and furthermore tends to undergo polymerization in the course of the distillization.

Ethylenecyanohydrin III can be suitably prepared by cleaving the bis-(2-cyanoethyl) ether II. According to JP-A No. 81 85 550, for this purpose the ether II is cleaved at from 120° to 200° C. in a weak base, such as tetraethylammonium acetate, to give ethylenecyanohydrin III and acrylonitrile. However, it is very difficult in this process to recover all of the acrylonitrile which tends to undergo polymerization.

According to DE-A No. 35 22 906, the ether II can be reacted with a methylate to give ethylenecyanohydrin III and 3-methoxypropionitrile. Although this process gives good yields, large amounts of 3-methoxypropionitrile, which is only of limited use, are inevitably obtained.

It is an object of the present invention to provide a process for the joint preparation of 3-dialkylaminopropionitrile I and bis-(2-cyanoethyl) ether II, which process does not have the deficiencies and disadvantages described, dispenses in particular with the working up of excess or unconverted acrylonitrile by distillation and permits, if desired, the preparation of ethylenecyanohydrin III from bis-(2-cyanoethyl) ether II, without this preparation having the disadvantages of the previous processes.

We have found that this object is achieved by a process for the joint preparation of 3-dialkylaminopropionitriles of the general formula I

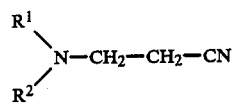

where $R^1$ and $R^2$ are each $C_1$-$C_4$-alkyl which may furthermore be bonded to form a 5-membered or 6-membered ring, bis(2-cyanoethyl) ether II $$NC-CH_2-CH_2-O-CH_2-CH_2-CN \qquad II$$

and, if desired, ethylenecyanohydrin III $$HO-CH_2-CH_2-CN \qquad III$$

wherein
(a) acrylonitrile and water are reacted in the presence of a base at from 60° to 150° C. to give a mixture of acrylonitrile, water and bis-(2-cyanoethyl) ether II, the base being a mineral base, a quaternary nitrogen base or a mixture of these,
(b) this mixture is reacted at about 0°-50° C. with a dialkylamine of the general formula IV

to give a mixture of water, a dialkylaminopropionitrile I and bis-(2-cyanoethyl) ether II, and this mixture is separated into its components and (c) if desired, the ether II obtained in process stage (b) or an aqueous solution of this ether and/or the reacted mixtures containing this ether and obtained from process stage a) or b) is allowed to react at from 50° to 150° C. with the dialkylamine IV to give a mixture of a 3-dialkylaminopropionitrile I and ethylenecyanohydrin III, and, if desired, the said mixture is separated into its components.

In process stage a), acrylonitrile is reacted with water in accordance with equation (1) to give bis(2-cyanoethyl) ether II. This reaction is catalyzed by bases.

Generally used bases are aqueous solutions of alkali metal hydroxides, in particular sodium hydroxide and potassium hydroxide, alkali metal carbonates, in particular sodium carbonate and potassium carbonate, and alkaline earth metal hydroxides. Particularly preferred bases are aqueous solutions of quaternary ammonium hydroxides, such as tetramethylammonium hydroxide, tetraethylammonium hydroxide, tetrapropylammonium hydroxide, tetrabutylammonium hydroxide, tetrapropylammonium hydroxide, dimethylbis-(hydroxyethyl)-ammonium hydroxide and tetrakis-(hydroxyethyl)-ammonium hydroxide. It is also possible to use quaternary ammonium hydroxides which carry long-chain alkyl radicals or benzyl radicals, or mixtures of quaternary ammonium hydroxides and mineral bases. It is furthermore possible to produce the quaternary ammonium hydroxides in the reaction medium from the corresponding ammonium salts by adding alkali metal or alkaline earth metal hydroxides. The base can be used in catalytic amounts, but it is also possible to use stoichiometric or excess amounts. The base is preferably used in catalytic amounts, i.e. in a ratio of base to acrylonitrile of from 1 to 0.001, in particular from 1 to 0.01 mol %.

To achieve a high conversion and a high yield of bis-(2-cyanoethyl) ether II, stoichiometric or excess amounts of water can be added. From 0.5 to 3.0, advantageously from 0.8 to 2, moles of water are preferably used per mole of acrylonitrile. Inert organic solvents, e.g. dioxane, tetrahydrofuran or ethylene glycol dimethyl ether may be added.

In general, the reaction of acrylonitrile with water is carried out in the presence of a base at from 60° to 150° C. Depending on the temperature chosen, the reaction is effected under atmospheric pressure (from 60° to 85° C.) or under autogenous pressure (from 80° to 150° C.). Temperatures of from 80° to 150° C., in particular from 90° to 140° C., are preferred. The reaction may be carried out either batchwise or continuously. If the reaction is carried out batchwise, it is advantageous to employ atmospheric pressure, whereas superatmospheric pressure is preferred in the case of the continuous process. The reaction is advantageously carried out by the continuous procedure under superatmospheric pressure.

In the continuous procedure, it is possible to use stirred reactor cascades or, preferably, stirred reactors. When stirred reactor cascades are used, residence times of from 15 minutes to 6 hours can be maintained; preferred residence times are from 30 minutes to 3 hours. If the reaction is effected in tube reactors, a residence time of the reaction mixture is chosen as 2-45, advantageously 3-30, minutes.

In the batchwise reaction, the acrylonitrile is generally initially taken and heated to 60°-70° C., the aqueous base solution is added while heating and the reaction mixture is kept at the desired reaction temperature until the required conversion has been reached. Advantageously, both in the batchwise and in the continuous process, only from 60 to 90, preferably from 70 to 85, % by weight of the acrylonitrile used is converted into bis-(2-cyanoethyl) ether II, since higher conversions are likely to give rise to increased byproduct formation due to hydrolysis reactions.

The reaction mixtures obtained in this process may contain up to 5% by weight of ethylenecyanohydrin.

To isolate the desired product 3-dialkylaminopropionitrile, according to the invention the reacted mixture from process stage a), which mixture contains not only acrylonitrile and bis-(2-cyanoethyl) ether I but also water and small amounts of ethylenecyanohydrin, is used in process stage (b) without being further worked up.

In process stage (b), the residual acrylonitrile is reacted with a dialkylamine IV to give a 3-dialkylaminopropionitrile I, in accordance with equation (2).

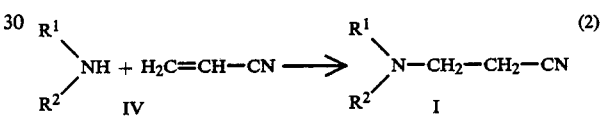

For this purpose, preferably molar amounts, based on acrylonitrile, of dialkylamino IV are generally added to the reacted mixture from process stage a), at from 0° to 50° C., preferably from 15° to 25° C., with cooling. Under these conditions, the acrylonitrile is converted virtually quantitatively into dialkylaminopropionitrile I in a short time. This process step can be carried out batchwise in stirred reactors or continuously, in stirred reactor cascades or preferably in tube reactors.

In principle, all $C_1$–$C_4$-dialkylamines having identical or different radicals $R^1$ and $R^2$ are suitable for the process. Examples are dimethylamine, diethylamine, dipropylamine, diisopropylamine, methylethylamine, dibutylamine and diisobutylamine. It is also possible to use secondary amines in which $R^1$ and $R^2$ together form a 5membered or 6-membered ring. Dimethylamine and diethylamine are preferably used.

The dialkylamines IV can be used either undiluted, in gaseous or liquid form, or in the form of solutions, preferably aqueous solutions.

The reaction mixture is advantageously worked up by the following procedure: the 3-dialkylaminopropionitrile I together with the water and the byproduct ethylenecyanohydrin III is isolated, for example, with the aid of a thin film evaporator. Thereafter, the remaining high boiling mixture is neutralized with a dilute mineral acid and the bis-(2-cyanoethyl) ether II is isolated from this mixture by fractional distillation under reduced pressure.

A particular advantage of the novel process is that it is easy to convert to enable 3-dialkylaminopropionitrile I and ethylenecyanohydrin III, instead of bis(2-cyanoethyl) ether II, to be obtained.

In this embodiment of the novel process, the bis(2-cyanoethyl) ether II present in the reacted mixture from process stage a) or b) is reacted, without prior isolation, at about 50°–150° C., with a dialkylamine IV, in accordance with equation (3), to give a 3-dialkylaminopropionitrile I and ethylenecyanohydrin III.

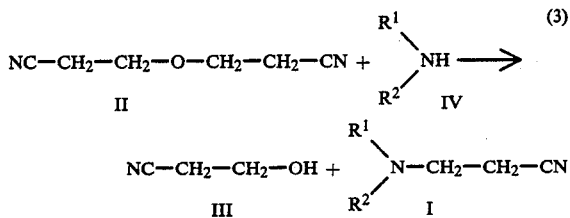

If the reacted mixture from process stage a) is used in this stage, the acrylonitrile present therein reacts with the dialkylamine IV under the conditions of ether aminolysis and accompanied by this reaction, in accordance with equation (2), to give the 3-dialkylaminopropionitrile IV. It is of course also possible to use the pure bis-(2-cyanoethyl) ether II, or a solution containing it, as the deduct in this process step.

In general, from 1 to 3, preferably from 1 to 1.5, moles of dialkylamine IV are used per mole of bis(2-cyanoethyl) ether II. If the reaction mixture still contains acrylonitrile, the amount of dialkylamine IV required to convert the acrylonitrile into 3-dialkylaminopropionitrile I is additionally introduced. Suitable dialkylamines IV are all dialkylamines stated in the description of process stage b), these being used either undiluted or in the form of a solution, advantageously an aqueous solution. Preferred dialkylamines IV are dimethylamine and diethylamine.

The aminolysis of the ether II begins at as low as 50° C. In this temperature range, however, the reaction rate is so low that reaction times of more than 5 hours are required. In general, the reaction is therefore carried out at above 50° C., advantageously at up to 150° C., preferably at from 80° to 130° C., in particular at from 100 to 130° C. Higher temperatures than 150° C. may be used but do not have any further advantages. The reaction can be carried out batchwise in stirred reactors or continuously in stirred reactor cascades or tube reactors, under atmospheric or superatmospheric pressure.

Particularly preferably, the reacted mixture from process stage (a) is reacted in the stated temperature ranges, in particular at from 100° to 130° C., during residence times of from 0.5 to 45, advantageously from 0.5 to 5, minutes, continuously and under superatmospheric pressure in a tube reactor.

A plurality of procedures are possible.

In general, the reacted mixture from process stage a) or b) is cooled to 0°–30° C., preferably 15°–25° C., and the corresponding dialkylamine IV is added to this reaction mixture. Since both aminolysis of the bis-(2-cyanoethyl) ether II and the accompanying formation of the 3-dialkylaminopropionitrile I from residual acrylonitrile are exothermic, the temperature of the reaction mixture automatically increases to the desired reaction temperature when the dialkylamine IV is added. In order to reduce the residence times required for complete conversion to 0.5–45 minutes, it is advantageous initially to heat the reaction mixture to 50°–80° C. after the addition of the dialkylamine IV. The reaction is maintained by the resulting heat of reaction.

In this procedure, it is possible to cool the reacted mixture a) or b) and to reheat the reaction mixture after the addition of the amine IV in a heat exchanger.

The temperature increase produced by the addition of the amine IV in the reaction mixture is of course dependent on the form of the amine is added. If, for example, a 40% strength by weight aqueous dimethylamine solution is added, the heat of reaction evolved corresponds roughly to the quantity of heat required to heat the reaction mixture to the desired temperature. If, on the other hand, liquid, undiluted dimethylamine is added, additional heat must be removed with the aid of cooling apparatuses in or on the reactor if the desired temperature range is not to be exceeded.

It is also possible to feed the amine IV to the reacted mixture from process stage (a) or (b) without cooling the said reacted mixture beforehand. If this procedure is applied to the reacted mixture from process stage (a), it is of course evident that in this case excess heat of reaction must be removed by cooling.

The cleavage of the ether II is generally carried out at from 50° to 150° C., preferably from 80° to 150° C. The reaction can be carried out batchwise in stirred reactors or continuously in stirred reactor cascades or in tube reactors, under atmospheric or superatmospheric pressure. Particularly preferably, the reacted mixture from process stage (a) is reacted at from 50° to 150° C., advantageously at from 100° to 130° C., for residence times of from 0.5 to 45, advantageously from 0.5 to 5, minutes, by continuous procedure and under superatmospheric pressure in a tube reactor.

The reacted mixture can be separated into its components in a conventional manner. Since the reacted mixture contains only very small amounts of impurities, it can, if desired, be further processed without further purification. For example, it is possible for the compounds contained in the reacted mixture, i.e. 3-dialkylaminopropionitrile I and ethylenecyanohydrin III, to be hydrogenated together in a hydrogenation stage to give the corresponding amines, or to be hydrolyzed with strong mineral bases to give the corresponding carboxylates.

In this process, ethylenecyanohydrin III can be obtained, in addition to 3-dialkylaminopropionitrile, in good yields.

EXAMPLE 1

A solution of 5.0 g (0.024 mole) of tetrakis-(hydroxyethyl)-ammonium hydroxide and 163 g (9.0 moles) of water was added to 600 g (11.3 moles) of acrylonitrile at 70° C. in the course of 45 minutes. This mixture was then stirred for 45 minutes at from 80° to 83° C.

After the resulting mixture had been cooled to 15°–20° C., it was mixed with 260 g of an aqueous 40% strength dimethylamine solution (2.3 moles) with cooling, and the mixture was stirred for 15 minutes.

A mixture of water, 3-dimethylaminopropionitrile and ethylenecyanohydrin was separated off from the resulting product mixture by means of a thin film evaporator at 90° C. and under 4 mbar and then separated into its components by fractional distillation. The high boiling liquid which remained at the bottom of the thin film evaporator was brought to a pH of 6 with dilute sulfuric acid and then subjected to fractional distillation under reduced pressure. The fraction boiling within a range of 125° to 140° C. under 3 mbar was collected.

Yield (based on acrylonitrile):
74.8% of bis-(2-cyanoethyl) ether 13.8% of 3-dimethylaminopropionitrile
7.6% of ethylenecyanohydrin

EXAMPLE 2

A solution of 1.85 g (0.009 mole) of tetrakis(hydroxyethyl)-ammonium hydroxide and 0.3 g (0.0075 mole) of sodium hydroxide in 261 g (14.5 moles) of water was added dropwise to 954 g (18 moles) of acrylonitrile at 70° C. in the course of 45 minutes. The stirred mixture was then heated at the boil for 75 minutes.

According to quantitative gas chromatographic analysis, the resulting reaction mixture contained 16% of acrylonitrile (conversion: 79.6%), 5.6% of ethylenecyanohydrin and 68% of bis-(2-cyanoethyl) ether (selectivity: 93.2%).

1536 g of a 40% strength by weight aqueous dimethylamine solution (13.7 moles) were added to this mixture while cooling at 15°–20° C. 689 g of the resulting mixture were heated to 80° C. and stirred at this temperature for 50 minutes.

After the end of the reaction, quantitative gas chromatographic analysis showed that the mixture contained 35.1% of 3-dimethylaminopropionitrile, 18% of ethylenecyanohydrin and 1.4% of bis-(2-cyanoethyl) ether. The total yield of ethylenecyanohydrin and 3-dimethylaminopropionitrile was 93.6%, based on acrylonitrile used.

The water was removed from the product mixture by azeotropic distillation with cyclohexane and the residue was then subjected to fractional distillation under reduced pressure.

Yield (based on acrylonitrile):
49.2% of 3-dimethylaminopropionitrile
36.3% of ethylenecyanohydrin

EXAMPLE 3

46.4 ml (0.71 mole) of acrylonitrile and a solution of 0.28 g (0.0013 mole) of tetrakis-(hydroxyethyl)ammonium hydroxide and 23.3 g (1.3 moles) of water were pumped per hour through a 23 ml tube reactor at 130° C. and under 6 bar.

263 g of a 40% strength by weight aqueous dimethylamine solution (2.3 moles) were added to 400 g of the reacted mixture at 20° C., while cooling, and the mixture was stirred for 1 hour at 80° C.

The product mixture was worked up as described in Example 2.

Yield (based on acrylonitrile):
44.8% of 3-dimethylaminopropionitrile
37.6% of ethylenecyanohydrin Acrylonitrile was converted into ethylenecyanohydrin and bis-(2-cyanoethyl) ether similarly to Example 2, after which a 40% strength aqueous dimethylamine solution was added to the mixture obtained. 689 g of the resulting mixture were pumped through a 23 ml tube reactor at 130° C., under 10 bar, and with a mean residence time of 1 minute.

Yield (according to quantitative gas chromatographic analysis and based on acrylonitrile):
57% of 3-dimethylaminopropionitrile
39.2% of ethylenecyanohydrin

EXAMPLE 5

A solution of 1.7 g (0.008 mole) of tetrakis-(hydroxyethyl)-ammonium hydroxide in 58 g (3.2 moles) of water was added to 212 g (4 moles) of acrylonitrile at 70° C. This mixture was then heated at 82° C. for 1 hour. The reaction mixture was cooled to 5° C., 99 g (2.2 moles) of liquid dimethylamine were added while cooling, and the resulting mixture was pumped through a 2.2 ml tube reactor at 130° C. and with a mean residence time of 3 minutes.

The reacted mixture was worked up by fractional distillation.

Yield (based on acrylonitrile):
48.9% of N,N-dimethylaminopropionitrile
33.8% of ethylenecyanohydrin

EXAMPLE 6

706.2 ml (10.8 moles) of acrylonitrile and a solution of 4.35 g (0.021 mole) of tetrakis-(hydroxyethyl)-ammonium hydroxide and 149.4 g (8.3 moles) of water were pumped per hour through a cascade consisting of two glass autoclaves having a volume of 315 ml and 320 ml, at 85° C. and under 6 bar, with thorough stirring, and the pressure was then let down to atmospheric pressure.

The reacted mixture was passed through a heat exchanger, 541 g (7.4 moles) of diethylamine were added per hour at 20° C. and the mixture was again heated to 70°–85° C. After leaving the heat exchanger, the reaction mixture was kept for another 1.5 hours in a further cascade at 70°–85° C. The reacted mixture was worked up by fractional distillation.

Yield (based on acrylonitrile):
52.3% of 3-diethylaminopropionitrile
28.6% of ethylenecyanohydrin

EXAMPLE 7

114 ml (92.3 g; 1.74 moles) of acrylonitrile and a solution of 0.84 g (0.004 mole) of tetrakis-(2-hydroxyethyl)-ammonium hydroxide in 29.2 g (1.6 moles) of water were pumped per hour through a 23 ml tube reactor at 100° C. and under 10 bar and then cooled to 20° C. in a heat exchanger. 199.8 ml/h (177.8 g/h) of a 40% strength aqueous dimethylamine solution (corresponding to 71.1 g; 1.58 moles of dimethylamine) were metered continuously into this mixture, and the resulting mixture was reacted in a second tube reactor having a volume of 8.5 ml, at 130° C., under 10 bar and with a mean residence time of 1.5 minutes.

The reacted mixture was worked up as described in Example 2.

Yield (based on acrylonitrile):
38% of ethylenecyanohydrin
56% of 3-dimethylaminopropionitrile.

What is claimed is:
1. A process for the joint preparation of
(1) an aminopropionitrile of the formula

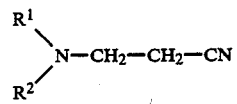

I where $R^1$ and $R^2$ are each $C_1$–$C_4$-alkyl or, when taken together, represent $C_4$–$C_5$-alkylene to form a 5-membered or 6-membered ring, (2) bis-(-b 2-cyanoethyl) ether

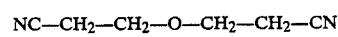   II, and (3) ethylenecyanohydrin

   III, which process comprises:
(a) reacting acrylonitrile and water in the presence of a base at from 60° to 150° C. to give a first product mixture containing acrylonitrile, water and said bis-(2-cyanoethyl) ether II, the base being selected from the group consisting of a mineral base, a quaternary nitrogen base, and mixtures thereof,
(b) reacting this first product mixture at about 0°–50° C. with a secondary amine of the formula

NH,          IV wherein $R^1$ and $R^2$ have the same meaning as above, to give a second product mixture containing water, said aminopropionitrile I and said bis-(2-cyanoethyl) ether II; and
(c) reacting said ether II obtained in at least one of the process stages (a) and (b) at from 50° to 150° C. with said amine IV to give a third product mixture containing said aminopropionitrile I and said ethylenecyanohydrin III.

2. A process for the joint preparation of
(1) an aminopropionitrile of the formula

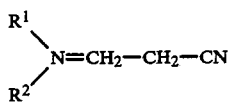N=CH$_2$—CH$_2$—CN     I where $R^1$ and $R^2$ are each $C_1$–$C_4$-alkyl or, when taken together, represent $C_4$–$C_5$-alkylene to form a 5-membered or 6-membered ring; and
(2) bis-(2-cyanoethyl) ether

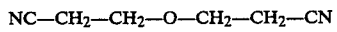
NC—CH$_2$—CH$_2$—O—CH$_2$—CH$_2$—CN     II, which process comprises:
(a) reacting acrylonitrile and water in the presence of a base at from 60° to 150° C. to give a first product mixture containing acrylonitrile, water and said bis-(2-cyanoethyl) ether II, the base being selected from the group consisting of a mineral base, a quaternary nitrogen base, and mixtures thereof; and
(b) reacting this first product mixture at about 0°–50° C. with a secondary amine of the formula

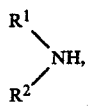NH,          IV wherein $R^1$ and $R^2$ have the same meaning as above, to give a second product mixture containing water, said aminopropionitrile I and said bis-(2-cyanoethyl) ether II.

3. A process as claimed in claim 2, which is carried out continuously under superatmospheric pressure in a tube reactor, and a residence of time of from 2 to 45 minutes is chosen for process stage (a) and a residence time of from 0.5 to 45 minutes is chosen for process stage (b).

4. A process as claimed in claim 1, which is carried out continuously under superatmospheric pressure in a tube reactor, and a residence time of from 2 to 45 minutes is chosen for process stage a) and residence times of from 0.5 to 45 minutes for process stages (b) and (c).

5. A process as claimed in claim 1, wherein the reacted mixture from process stage (a) is cooled to 0°–30° C. before being transferred to process stage (c), after which the secondary amine IV is fed in and the resulting heat of reaction is used for heating the reaction mixture to 50°–150° C.

6. A process as claimed in claim 1, wherein the reacted mixture from process stage (a) or (b) is cooled to 0°–30° C. before being transferred to process stage c), after which the secondary amine IV is fed in and then the reaction mixture is heated to 50°–80° C. and the resulting heat of reaction is used for further heating of the reaction mixture.

7. A process as claimed in claim 1, wherein the reacted mixture from process stage (a) or (b) is cooled to 20°–25° C. before being transferred to process stage (c).

8. A process as claimed in claim 1, wherein the reacted mixture from process stage (a) or (b) is combined with the secondary amine IV without prior cooling.

* * * * *